United States Patent [19]

Flynn et al.

[11] Patent Number: 5,100,917
[45] Date of Patent: Mar. 31, 1992

[54] NOVEL A-NOR-STEROID-3-CARBOXYLIC ACID DERIVATIVES

[75] Inventors: Gary A. Flynn; Philippe Bey, both of Cincinnati; Thomas R. Blohm, Maderia, all of Ohio

[73] Assignee: Merrell Dow Pharmaceuticals Inc., Cincinnati, Ohio

[21] Appl. No.: 580,759

[22] Filed: Sep. 11, 1990

Related U.S. Application Data

[63] Continuation-in-part of Ser. No. 458,869, Dec. 29, 1989, abandoned.

[51] Int. Cl.$^5$ ............................................. A61K 31/21
[52] U.S. Cl. .................................... 514/510; 514/562; 514/563; 514/573; 560/10; 560/37; 560/48; 560/116; 562/427; 562/457; 562/498
[58] Field of Search ............... 560/116, 10, 37, 48; 562/498, 427, 457; 514/510, 562, 563, 573

[56] References Cited

U.S. PATENT DOCUMENTS

| | | | |
|---|---|---|---|
| 3,336,338 | 8/1967 | Rosenthal | 560/116 |
| 3,424,751 | 1/1969 | Scribner | 560/116 |
| 3,484,476 | 12/1969 | Rosenthal | 560/116 |
| 3,492,359 | 1/1970 | Diassi | 560/116 |
| 3,600,425 | 8/1971 | Fried | 560/116 |
| 4,910,226 | 3/1990 | Holt et al. | 514/573 |

FOREIGN PATENT DOCUMENTS 0289327 11/1988 European Pat. Off. .

OTHER PUBLICATIONS

"Hackh's Chemical Dictionary," 4th Ed., p. 27 (1969).

*Primary Examiner*—Michael L. Shippen
*Attorney, Agent, or Firm*—Louis J. Wille

[57] ABSTRACT

The present invention relates to novel A-nor-steroid-3-carboxylic acid derivatives and to their use as inhibitors of mammalian 5α-reductase.

15 Claims, No Drawings

NOVEL A-NOR-STEROID-3-CARBOXYLIC ACID DERIVATIVES

BACKGROUND OF THE INVENTION

This is a continuation-in-part of application Ser. No. 458,869, filed Dec. 29, 1989, now abandoned. The present invention relates to novel A-nor-steroid-3-carboxylic acid derivatives and to their use as inhibitors of mammalian steroid 5-α-reductase.

Mammalian steroid 5-α-reductase is an enzyme present in mammalian tissues, including skin, male genitalia and prostate gland, which catalyzes the conversion of the steroidal hormone testosterone to the steroidal hormone dihydrotestosterone (5-α-androstane-17-β-ol-3-one). Testosterone and dihydrotestosterone (DHT) are members of the class of hormones called androgens which are primarily responsible for producing the physical characteristics which differentiate males from females. Testosterone and DHT are the primary androgenic steroids in males. However DHT, rather than testosterone, is the most potent androgen end-organ effector in certain tissues, particularly in mediating growth. Furthermore, DHT is formed mostly in the target cells themselves by reduction of testosterone by 5-α-reductase.

It is known that skin responds to androgens and is an active site of androgen metabolism. In particular, testosterone is metabolized in the skin to DHT by the action of 5-α-reductase. Testosterone metabolism in the skin may at times be abnormally excessive and have undesirable effects. There is considerable evidence that DHT is involved in the pathogenesis of acne, including acne vulgaris, as well as other androgen associated conditions [See Price, Arch. Dermatol. 111, 1496 (1975)]. Agents which are capable of blocking the formation of DHT from testosterone in skin, such as by inhibiting the activity of 5-α-reductase, would therefore be effective in the treatment of acne.

In addition, other physical conditions and disease states, including benign prostatic hypertrophy, androgenetic alopecia (common baldness caused by androgen in genetically susceptible men and women), seborrhea and female hirsutism, are associated with elevated androgen activity. Agents which are capable of blocking the formation of DHT from testosterone would also be effective in the treatment of these conditions.

SUMMARY OF THE INVENTION

The present invention provides novel A-nor-steroid-3-carboxylic acid derivatives of the formula (A), (B), (C) or (D)

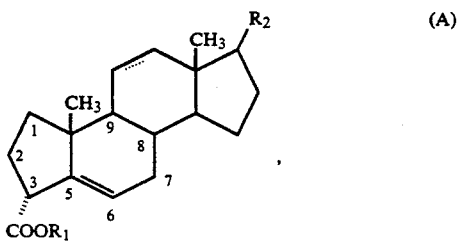

(A)

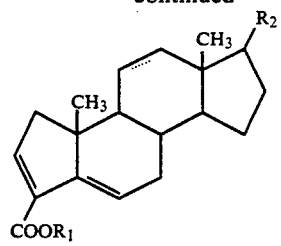

(B)

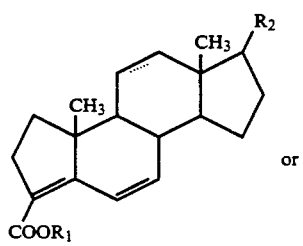

(C)

or

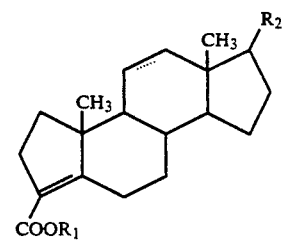

(D)

wherein
the dotted line represents an optional double bond;
$R_1$ is hydrogen, $C_1$-$C_6$ alkyl or —$(CH_2)_x$-Ar-$(M)_y$, wherein x is 0, 1 or 2, Ar is phenyl y is 0, 1 or 2, and M is $C_1$-$C_6$ alkoxy, halogen, $C_1$-$C_6$ alkyl or -$S(O)_zR_5$ wherein $R_5$ is a $C_1$-$C_6$ alkyl and z is 0, 1 or 2; and
$R_2$ is $C_1$-$C_6$ alkanol; $C_1$-$C_6$ alkanone, $CON(R_3)(R_4)$, wherein $R_3$ and $R_4$ are each independently, hydrogen or $C_1$-$C_6$ alkyl, or —$(CH_2)_x$-Ar-$(M)_y$, wherein x is 0, 1 or 2, Ar is phenyl, y is 0, 1 or 2, and M is $C_1$-$C_6$ alkoxy, halogen, $C_1$-$C_6$ alkyl, or —$Si(O)_zR_5$ wherein $R_5$ is a $C_1$-$C_6$ alkyl and z is 0, 1 or 2.

The present invention also provides a method of inhibiting 5-α-reductase in a patient in need thereof, comprising administering to said patient a therapeutically effective 5-α-reductase inhibiting amount of a compound of formula (A), (B), (C), (D).

DETAILED DESCRIPTION OF THE INVENTION

The term "$R_1$" is defined to be hydrogen, a $C_1$-$C_6$ alkyl or —$(CH_2)_x$-Ar-$(M)_y$. As used herein, the terms "$C_1$-$C_6$ alkyl" and "$C_1$-$C_6$ alkyl/cycloalkyl" refers to a saturated alkyl group of from 1 to 6 carbon atoms of straight, branched or cyclic configuration. Included within the scope of this term are methyl, ethyl, n-propyl, isopropyl, butyl, isobutyl, tertiarybutyl, pentyl, hexyl, cyclohexyl and the like. The moiety "—$(CH_2)_x$—" refers to a straight chain alkylene radical wherein x is 0, 1 or 2. The term "-Ar-$(M)_y$," refers to a phenyl or a napthyl group which can be unsubstituted (y=0), mono-substituted (y=1) or di-substituted (y=2) with the substituents described by the term "M". The term "M" refers to $C_1$-$C_6$ alkoxy, halogen, $C_1$-$C_6$ alkyl, or —$S(O)_zR_5$ moieties.

As used herein, the term "$C_1$-$C_6$ alkoxy" refers to a saturated alkyl group of from 1 to 6 carbon atoms of straight, branched or cyclic configuration bearing an oxygen radical. Included within the scope of this term are methoxy, ethoxy, propoxy, isopropoxy, butoxy, isobutoxy, tertiarybutoxy, pentoxy, hexoxy, cyclohexyloxy and the like. As used herein, the term "halogen" or "halo" refers to a fluorine, chlorine, bromine or iodine radical.

As used herein, the term "$C_1$-$C_6$ alkanol" and $C_1$-$C_6$ alkyl alcohol refers to a saturated alkyl group of from 1 to 6 carbon atoms of straight, branched or cyclic configuration bearing a hydroxy group. Included within the scope of this term are the following groups: —$CH_2OH$; —$CH(OH)CH_3$; —$C(CH_3)_2OH$; —$CH(OH)CH_2CH_3$; —$CH(OH)CH_2CH(CH_3)_2$; —$CH(CH_3)CH_2OH$;

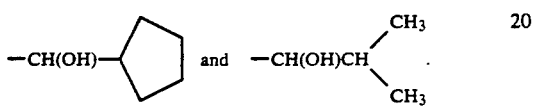

As used herein, the terms "$C_1$-$C_6$ alkanone" and "$C_1$-$C_6$ alkyl aldehyde/ketone" refer to a saturated alkyl group of from 1 to 6 carbon atoms of straight, branched or cyclic configuration bearing a double-bonded oxygen atom. Included within the scope of this term are the following groups: —CH=0; —C(0)CH$_3$; —CH(0)CH$_2$CH$_3$; —CH(0)CH(CH$_3$)2;

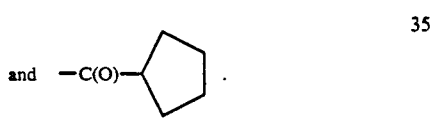

As used herein, the term "CON($R_3$)($R_4$)" refers to a hydrogen, $C_1$-$C_6$ alkyl or —$(CH_2)_x$-Ar-$(M)_y$ as defined above.

The A-nor-steroid-3-carboxylic acid derivatives of the present invention, i.e. compounds of formulas (A), (B), (C) and (D), can be prepared by utilizing conventional procedures and techniques which are well known and appreciated in the art.

A general synthetic procedure for the preparation of compounds of formula (A) is set forth in Scheme A. In Scheme A, all substituents are as previously defined. In addition, the term "$R_1$'" refers to all those moieties defined by $R_1$ other than hydrogen.

SCHEME A

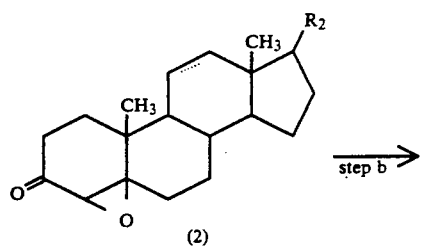

-continued
SCHEME A

-continued
SCHEME A

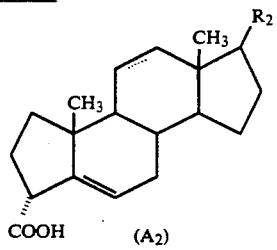

In general, an appropriate compound of formula (A) can be prepared in a 5-step process from the appropriate steroid derivative of structure (1).

In step a, the olefin functionality of the appropriate steroid derivative of structure (1) is oxidized to the corresponding epoxide functionality. For example, the epoxy steroid derivative of structure (2) can be prepared by oxidizing the steroid derivative of structure (1) with hydrogen peroxide in the presence of a base, such as sodium hydroxide, in a suitable solvent system, such as a mixture of tetrahydrofuran and methanol.

In step b, the epoxide functionality of the epoxy steroid derivative of structure (2) is converted to the corresponding methyl enol ether functionality. For example, the methyl enol ether steroid of structure (3) can be prepared by the enol ether addition/elimination of the epoxide functionality of the steroid derivative of structure (2) with sodium methoxide, in a suitable alcoholic solvent, such as methanol.

In step c, the ketone functionality of the methyl enol ether steroid of structure (3) is reduced to the corresponding alcohol functionality. For example, the methyl enol ether steroid of structure (3) can be reduced to the corresponding hydroxy steroid derivative of structure (4) with sodium borohydride in a suitable protic solvent, such as ethanol.

In step d, the hydroxy steroid derivative of structure (4) is converted to the corresponding 4-keto-$\Delta^5$-steroid derivative of structure (5). For example, the hydroxy steroid derivative of structure (4) can be hydrolyzed to the corresponding 4-keto-$\Delta^5$-steroid derivative of structure (5) with a suitable acid, such as perchloric acid, in a suitable solvent mixture, such as methylene chloride and acetonitrile.

In step e, the A-nor-$\Delta^5$-steroid-3-carboxylic acid ester of formula ($A_1$) can be prepared by treating the appropriate 4-keto-$\Delta^5$-steroid derivative of structure (5) with a reagent having a hypervalent iodine in the presence of an appropriate alcohol ($R_1$'OH) and a base. This treatment results in a ring contraction and an esterification of the 4-keto-$\Delta^5$-steroid derivative of structure (5) to yield the corresponding A-nor-$\Delta^5$-steroid-3-carboxylic acid ester derivative ($A_1$).

Treatment of the 4-keto-$\Delta^5$-steroid derivative (5) with a base results in the formation of the corresponding cross conjugated dienolate. The preferred strong bases for this reaction are hydroxides of an alkali earth metals such as potassium hydroxide and sodium hydroxide.

The cross conjugated enolate is then subjected to an electrophilic addition of a hypervalent iodine or a thallium$^{III}$ salt at the 3-position of the enolate. Addition of a hypervalent iodine is preferred. Reagents having a hypervalent iodine which are useful in this reaction are reagents such as iodosobenzene. Iodosobenzene is the preferred reagent for use in the above described reaction. Iodosobenzene can be prepared by procedures well known and appreciated in the art. It can be added to the reaction mixture directly or it can be formed in situ by adding a precursor such as iodobenzenediacetate to the reaction mixture containing the base.

The alcohol ($R_1$'OH) present in the reaction mixture attacks the 3-keto group yielding the corresponding A-nor-$\Delta^5$-steroid-3-carboxylic acid ester derivative ($A_1$). Where a compound of the present invention is desired wherein $R_1$ is a substituent other than hydrogen, the appropriate alcohol ($R_1$'OH) is selected to provide the desired substituent $R_1$' in the final product For example, where a compound of formula (A) is desired wherein $R_1$ is ethyl, ethanol is used in step e. Likewise, where a compound of formula (A) is desired wherein $R_1$ is benzyl, hydroxymethylbenzene can be used in step e. Alternatively, compounds of formula (A) wherein $R_1$ is not hydrogen can be prepared from the compounds of formula (A) wherein $R_1$ is hydrogen by conventional esterification procedures and techniques which are well known in the art.

In step f, the ester functionality of the appropriate A-nor-$\Delta^5$-steroid-3-carboxylic acid ester derivative ($A_1$) can be converted to the corresponding carboxylic acid functionality under carefully controlled conditions. For example, the appropriate A-nor-$\Delta^5$-steroid-3-carboxylic acid ester derivative ($A_1$) can be converted to the corresponding A-nor-$\Delta^5$-steroid-3-carboxylic acid ($A_2$) under non-hydrolytic conditions, such as reaction with trimethylsilyl iodide, in a suitable aprotic solvent, such as methylene chloride.

The starting steroid derivative (1) is selected to provide the desired substituent as $R_2$ in the final product. Steroid derivatives with the appropriate substituent for $R_2$ are either readily available or can be prepared from available derivatives using procedures and techniques which are well known and appreciated by those of ordinary skill in the art.

The following examples present typical syntheses as described by Scheme A. These examples are understood to be illustrative only and are not intended to limit the scope of the invention in any way. As used in the following examples, the following terms have the meanings indicated: "g" refers to grams, "mmol" refers to millimoles, "mL" refers to milliliters, "° C." refers to degrees Celsius, "TLC" refers to thin layer chromatography, "mg" refers to milligrams, "THF" refers to tetrahydrofuran, "$\mu$L" refers to microliters, "HPLC" refers to high pressure liquid chromatography.

Furthermore, with respect to the nomenclature of specific compounds as named herein, the term "20$\alpha$" refers to a compound with an S-absolute configuration at the 20-position.

EXAMPLE 1

17$\beta$-(N,N-Diisopropylcarboxamide)-A-nor-androst-5-ene-3$\alpha$-carboxylic acid and methyl ester Step a:

17$\beta$-(N,N-Diisopropylcarboxamide)-androst-4,5-epoxy-3-one

Mix 3-oxo-4-androstene-17$\beta$-carboxylic acid (11.2g, 35.4mmol) and methylene chloride (100mL), place under a nitrogen atmosphere and cool to 0° C. with an ice-bath. Add triethylamine (4.1 g, 40.6 mmol), followed by dropwise addition of oxalyl chloride (3.8 mL, 4.4 mmol). Allow to warm to 25° C. and stir for 30 minutes. Cool the reaction mixture to 0° C. and add, by dropwise addition, additional oxalyl chloride (2.91 g, 22.9 mmol). Allow to warm to 25° C. and stir for 1 hour. Cool to 0° C. and add, by dropwise addition, diisopropylamine (23.7 mL, 169 mmol), keeping the temperature below 40° C. Stir at 25° C. overnight, add ice water and separate the organic phase. Extract the aqueous phase with ethyl acetate (2X), wash the combined organic phases with 10% hydrochloric acid, 10% potassium hydroxide, water, then saturated sodium chloride. Dry and evaporate the solvent in vacuo to give the crude product. Purify by silica gel chromatography to give 17β-(N,N-diisopropylcarboxamide)-androst-4-ene-3-one.

Dissolve 17β-(N,N-diisopropylcarboxamide)-androst-4-ene-3-one (10 g, 25 mmol) in tetrahydrofuran (40 mL) and methanol (25 mL). Cool to 5° C. and treat with 30% hydrogen peroxide (10.8 mL) and 10% sodium hydroxide (5 mL). When reaction is complete, evaporate the solvent in vacuo without heat, and take up the residue in ethyl acetate/water. Separate the organic phase, wash well with water, then with saturated sodium chloride. Dry (MgSO$_4$) and evaporate the solvent in vacuo to give 10.5 g of the crude title epoxides.

Step b:

17β-(N,N-Diisopropylcarboxamide)-androst-4-ene 4-methoxy-3-one

Dissolve sodium hydroxide (10 g) in hot methanol (125 m) and heat to reflux. Add, with stirring, 17β-(N,N-diisopropylcarboxamide)-androst-4,5-epoxy-3-one (10.5 g) in methanol (10 mL). Stir for 15 minutes, pour into water and extract into ethyl acetate. Separate the organic phase, wash with water and dry. Evaporate the solvent in vacuo and purify by silica gel chromatography (25% ethyl acetate/hexane) to give 1.5 g of the title compound as a crystalline solid; mp 223–225° C.

NMR-ppm δ(CDCl$_3$) 300MHz: 4.19 (h, 1H, J=7Hz); 3.60 (s, 3H); 3.40 (h, 1H, J=7Hz); 3.08 (dt, 1H, J$_d$=10Hz, J$_t$=2Hz); 2.63 (t, 1H, J=7Hz); 1.43 (d, 3H, J=7Hz); 1.40 (d, 3H, J=7Hz); 1.23 (d, 3H, J=7Hz); 1.21 (2, 3H); 1.15 (d, 3H, 7Hz); 0.82 (s, 3H).

Step c:

17β-(N,N-Diisopropylcarboxamide)-androst-4-ene-4-methoxy-3-ol

Dissolve 17β-(N,N-diisopropylcarboxamide)-androst-4 ene 4-methoxy-3-one (2.0 g, 4.6 mmol) in absolute ethanol (20 mL) and place under nitrogen atmosphere. Treat with sodium borohydride (100 mg) for 2 hours at 25° C. Add water and stir for 30 minutes. Pour the solution into ethyl acetate, separate the organic phase and wash well with water. Dry (MgSO$_4$) and evaporate the solvent in vacuo to give 1.9 g of the title compound as a solid.

Step d:

17β-(N,N-Diisopropylcarboxamide)-androst-5-ene-4-one

Dissolve 17β-(N,N-Diisopropylcarboxamide)-androst-4-ene 4-methoxy-3-ol in freshly distilled acetonitrile (20 mL) and anhydrous methylene chloride (15 mL). Add 70% perchloric acid (4 drops) and stir at 25° C. After 10 minutes, pour the yellow solution into saturated sodium hydrogen carbonate and extract into methylene chloride. Separate the organic phase and dry (MgSO$_4$). Purify by silica gel chromatography (20% ethyl acetate/hexane) to give 1.0 g of the title compound; mp 138°–189° C. NMR-ppm δ(CDCl$_3$) 300MHz: 6.42 (dd, 1H, J$_1$=5Hz, J$_2$=3Hz); 4.23 (h, 1H, J=7Hz); 3.39 (h, 1H, J=7Hz); 2.64 (t, 1H, J=7Hz); 1.42 (d, 3H, J=7Hz); 1.37 (d, 3H, J=7Hz); 1.22 (d, 3H, J=7Hz); 1.13 (d 3H J=7Hz); 0.96 (s, 3H); 0.78 (s, Step e:

17β-(N,N-Diisopropylcarboxamide)-A-nor-androst-5-ene-3o-carboxylic acid, methyl ester Dissolve potassium hydroxide (110 mg) in anhydrous methanol (2 mL), place under a nitrogen atmosphere and cool to 0° C. Add 17β-(N,N-diisopropylcarboxamide)-androst-5-ene-4-one (120 mg, 0.30 mmol), followed by iodobenzene diacetate (200 mg, 0.60 mmol). Stir the light yellow solution for 1 hour at 0°–5° C. and pour into dilute hydrochloric acid. Extract into methylene chloride, separate the organic phase and dry (MgSO$_4$). Evaporate the solvent in vacuo and treat the residue with excess diazomethane. Evaporate the solvent in vacuo to give the title compound as a yellow film.

NMR-ppm δ(CDCl$_3$) 300MHz: 5.48 (m, 1H); 4.23 (h, 1H, J=7Hz); 3.70 (s, 3H); 3.41 (h, 1H, J=7Hz); 2.65 (t, 1H, J=7Hz); 1.43 (d, 3H, J=7Hz); 1.40 (d, 3H, J=7Hz); 1.22 (d, 1H, J=7Hz); 1.15 (d, 3H, J=7Hz); 0.95 (s, 3H); 0.78 (s, 3H).

Step f:

17β-(N,N-Diisopropylcarboxamide)-A-nor-androst-5-ene-3α-carboxylic acid

Dissolve 17β-(N,N-diisopropylcarboxamide)-A-nor-androst-5-ene-3α-carboxylic acid, methyl ester (100 mg, 0.233 mmol) in methylene chloride (3 mL) and treat with trimethylsilyl iodide (78 mg, 0.5 mmol). When the reaction is complete, pour the reaction mixture into buffer and separate the organic phase. Wash the organic phase with well with water, dry (MgSO$_4$) and evaporate the solvent in vacuo. Purify by silica gel chromatography to give the title compound.

EXAMPLE 2

17β-(N-t-Butylcarboxamide)-A-nor-androst-5-ene-3α-carboxylic acid and isopropyl ester Step a:

17β-(N-t-Butylcarboxamide)-androst-4,5-epoxy-3-one

Mix 3-oxo-4-androstene-17β-carboxylic acid (11.2 g, 35.4 mmol) and methylene chloride (100 mL), place under a nitrogen atmosphere and cool to 0° C. with an ice-bath. Add triethylamine (4.1 g, 40.6 mmol), followed by dropwise addition of oxalyl chloride (3.8 mL, 4.4 mmol). Allow to warm to 25° C. and stir for 30 minutes. Cool the reaction mixture to 0° C. and add, by dropwise addition, additional oxalyl chloride (2.91 g, 22.9 mmol). Allow to warm to 25° C. and stir for 1 hour. Cool to 0° C. and add, by dropwise addition, t-butylamine (17.8 mL, 169 mmol), keeping the temperature below 40° C. Stir at 25° C. for 30 minutes, add ice water and separate the organic phase. Extract the aqueous phase with ethyl acetate (2X), wash the combined organic phases with 10% hydrochloric acid, 10% potassium hydroxide, water, then saturated sodium chloride. Dry and evaporate the solvent in vacuo to give 13.4 g of a yellow solid. Purify by silica gel chromatography (6:4 ethyl acetate/hexane increasing polarity to 4:6 ethyl acetate/hexane) to give 7.9 g (60%) of 17β-(N-t-butylcarboxamide)-androst-4-ene-3-one; mp 226–227° C.

NMR-ppm δ(CDCl₃) 300MHz: 5.72 (s, 1H); 5.07 (bs, 1H); 1.34 (s, 9H); 1.17 (s, 3H); 0.82 (s, 3H).

Dissolve 17β-(N-t-butylcarboxamide)-androst-4-ene-3-one (8.5 g, 23 mmol) in tetrahydrofuran (100 mL) and methanol (100 mL). Cool to 0° C. and treat with 30% hydrogen peroxide (34 mL) and 10% sodium hydroxide (10 mL). Stir at 0° C. for 4 hours, store at −4° C. for 12 hours, then stir at 0°–5° C. for 4 hours. Pour into methylene chloride and water and separate the organic phase. Extract the aqueous phase with methylene chloride, combine the organic phases, and wash with water. Dry (MgSO₄) and evaporate the solvent in vacuo to give 8.7 g of the crude title epoxides.

Step b:

17β-(N-t-Butylcarboxamide)-androst-4-ene-4-methoxy-3-one

Dissolve sodium hydroxide (8 g) in hot methanol (120 mL) and heat to reflux under a nitrogen atmosphere. Add, with stirring, crude 17β-(N-t-butylcarboxamide)-androst-4,5-epoxy-3-one (8.7 g) in methanol (20 mL). Reflux for 10 minutes, pour into water and extract into methylene chloride. Separate the organic phase and dry. Evaporate the solvent in vacuo and purify by silica gel chromatography to give 2.0 g of the title compound as a solid; mp 190°–3° C.

NMR-ppm δ(CDCl₃) 300MHz: 5.10 (bs, 1H); 3.61 (s, 3H); 3.08 (dt, 1H, $J_d$=12Hz, $J_t$=2Hz); 1.37 (s, 9); 1.21 (s, 3H); 0.84 (s, 3H):

Step c:

17β-(N-t-Butylcarboxamide)-androst-4-ene-4-methoxy-3-ol

Dissolve 17β-(N-t-butylcarboxamide)-androst-4-ene-4-methoxy-3-one (2.0 g) in absolute ethanol (20 mL). Treat with sodium borohydride (200 mg) for 2 hours at 25° C. Add water and pour into methylene chloride. Separate the organic phase and wash with water, dry (MgSO₄) and evaporate the solvent in vacuo to give 2.1 g of the title compound as a foam.

Step d:

17β-(N-t-Butylcarboxamide)-androst-5-ene-4-one

Dissolve 17β-(N-t-butylcarboxamide)-androst-4-ene-4-methoxy-3-ol (2.1 g) in freshly distilled acetonitrile (8 mL) and anhydrous methylene chloride (25 mL). Add 70% perchloric acid (2 drops) and stir at 25° C. After 15 minutes, pour the solution into saturated sodium hydrogen carbonate and extract into methylene chloride. Separate the organic phase and dry (MgSO₄). Purify by silica gel chromatography (30%–50% ethyl acetate/hexane) to give 1.0 g of the steroid. Purify further by silica gel chromatography (25% ethyl acetate/hexane) to give 460 mg of the title compound as a foam.

NMR-ppm δ(CDCl₃) 300MHz: 6.43 (dd, 1H, $J_1$=5Hz, $J_2$=3Hz); 5.12 (bs, 1H); 1.36 (s, 9H); 0.96 (s, 3H); 0.82 (s, 3H).

Step e:

17β-(N-t-Butylcarboxamide)-A-nor-androst-5-ene-3α-carboxylic acid, isopropyl ester Dissolve potassium hydroxide (110 mg) in isopropanol (3 mL), place under a nitrogen atmosphere and cool to 0° C. Add 17β-(N-t-butylcarboxamide)-androst-5-ene-4-one (112 mg, 0.30 mmol), followed by iodobenzene diacetate (200 mg, 0.60 mmol). Stir the solution for 2 hours at 0°–5° C. and pour into ethyl acetate. Separate the organic phase, wash with water and dry (MgSO₄). Evaporate the solvent in vacuo and purify by silica gel chromatography to give 50 mg of the title compound and its 3β-isomer which can be separated by chromatography.

NMR-ppm δ(CDCl₃) 300MHz: 5.55 (m, 1H); 5.02 (h, 1H, J=7Hz); 3.30 (dd, 1H, $J_1$=7Hz, $J_2$=6Hz); 1.37 (s, 9H); 1.25 (d, 6H, J=7Hz); 0.95 (s, 3H); 0.82 (s, 3H).

Step f:

17β-(N-t-Butylcarboxamide)-A-nor-androst-5-ene-3α-carboxylic acid

Dissolve 17β-(N-t-butylcarboxamide)-A-nor-androst-5-ene-3α-carboxylic acid, isopropyl ester (100 mg, 0.2 mmol) in methylene chloride (3 mL) and treat with trimethylsiliyl iodide (78 mg, 0.5 mmol). When the reaction is complete, pour the reaction mixture into buffer and separate the organic phase. Wash the organic phase well with water, dry (MgSO₄) and evaporate the solvent in vacuo. Purify by silica gel chromatography to give the title compound.

A general synthetic procedure for an alternate preparation of steroid derivatives of formula (A), wherein $R_1$ is hydrogen, and for the preparation of steroid derivatives of formula (D), wherein $R_1$ is hydrogen, is presented in Scheme B. In Scheme B, all substituents are as previously defined.

SCHEME B

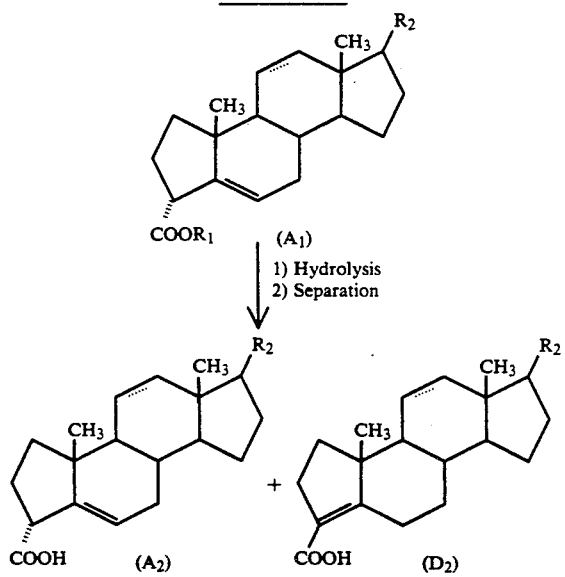

In general, steroid derivatives of formula (A), wherein $R_1$ is hydrogen, and steroid derivatives of formula (D), wherein $R_1$ is hydrogen, can be prepared by hydrolysis of the appropriate 4-nor-Δ⁵-3-carboxylic acid ester derivative of formula (A₁), followed by separation of the resulting mixture of steroid derivatives. The preferred base for such hydrolysis is one, such as lithium hydroxide, which would tend to preserve the sterio-orientation of the α-carboxylic acid at the 3-position. The steroid derivatives of formula (A), wherein $R_1$ is hydrogen, and steroid derivatives of formula (D), wherein $R_1$ is hydrogen, can then be separated by techniques and procedures well known and appreciated in the art, such as by High Performance Liquid Chromatography (HPLC).

The following examples present typical syntheses as described by Scheme B. These examples are understood to be illustrative only and are not intended to limit the scope of the present invention in any way.

EXAMPLE 3

17β-(N,N-Diisopropylcarboxamide)-A-nor-androst-5-ene-3α-carboxylic acid and
17B—(N,N-Diisopropylcarboxamide)-A-nor-androst-3-ene-3o-carboxylic acid Dissolve 17β-(N,N-diisopropylcarboxamide)-A-norandrost-5-ene-3α-carboxylic acid, methyl ester (100 mg, 0.233 mmol) in ethanol (4 mL) and treat with lithium hydroxide (42 mg, 10 mmol) and water (1 mL). Stir under nitrogen atmosphere until hydrolysis is complete, evaporate the solvent, acidify with dilute hydrochloric acid and extract into ethyl acetate. Separate the organic phase, extract the aqueous phases with ethyl acetate (2X) and wash the combined organic phases with water, then with saturated sodium chloride. Dry (MgSO4), evaporate the solvent in vacuo and separate by HPLC to give the title compounds.

EXAMPLE 4

17β-(N-t-Butylcarboxamide)-A-nor-androst-5-ene-3α-carboxylic acid and
17β-(N-t-Butylcarboxamide)-A-nor-androst-3-ene-3-carboxylic acid Dissolve 17β-(N-t-butylcarboxamide)-A-norandrost-5-ene-3α-carboxylic acid, isopropyl ester (100 mg, 0.233 mmol) in ethanol (4 mL) and treat with lithium hydroxide (42 mg, 10 mmol) and water (1 mL). Stir under nitrogen atmosphere until hydrolysis is complete, evaporate the solvent, acidify with dilute hydrochloric acid and extract into ethyl acetate. Separate the organic phase, extract the aqueous phases with ethyl acetate (2X) and wash the combined organic phases with water, then with saturated sodium chloride. Dry (MgSO4), evaporate the solvent in vacuo and separate by HPLC to give the title compounds.

The following compounds can be prepared by procedures analogous to those described in Example 1-4:

20α-(hydroxymethyl)-A-nor-pregn-5-ene-3α-carboxylic acid;
20α-(hydroxymethyl)-A-nor-pregn-5,11-diene-3α-carboxylic acid;
A-nor-pregn-5-ene-20-one-3α-carboxylic acid;
A-nor-pregn-5,11-diene-20-one-3α-carboxylic acid;
17β-(N-tertiarybutylcarboxamide)-A-nor-androst-5-ene-3α-carboxylic acid;
17β-(N-tertiarybutylcarboxamide)-A-nor-androst-5,11-diene-3α-carboxylic acid;
17β-(N,N-diisopropylcarboxamide)-A-nor-androst-5,11-diene-3α-carboxylic acid.
20α-(hydroxymethyl)-A-nor-pregn-3-ene-3-carboxylic acid;
20α-(hydroxymethyl)-A-nor-pregn-3,11-diene-3-carboxylic acid;
A-nor-pregn-3-ene-20-one-3-carboxylic acid;
A-nor-pregn-3,11-diene-20-one-3-carboxylic acid;
17β-(N,N-diisopropylcarboxamide)-A-nor-androst-3,11-diene-3-carboxylic acid;
17β-(N-tertiarybutylcarboxamide)-A-nor-androst-3-ene-3-carboxylic acid;
17β-(N-tertiarybutylcarboxamide)-A-nor-androst-3,11-diene-3-carboxylic acid.

A general synthetic procedure for the preparation of compounds of formula (B) is presented in Scheme C. In Scheme C, all substituents are as previously defined. In addition, the term "φSe" refers to a phenylselenyl group; the term "Z" refers to either a counterion of a metal or a trimethylsilyl radical; the term "X" refers to a halogen radical.

SCHEME C

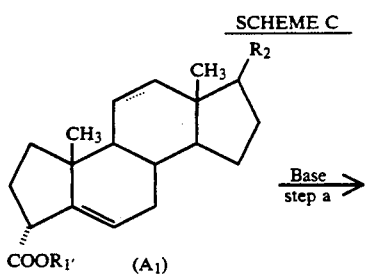

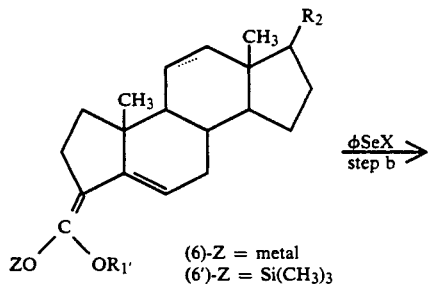

(6)-Z = metal
(6')-Z = Si(CH3)3

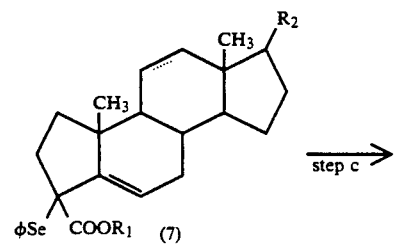

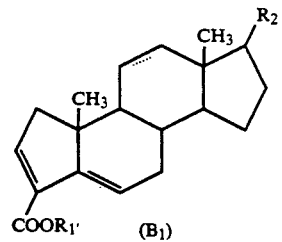

In general, steroid derivatives of formula (B) can be prepared in a 3-step process from steroid derivatives of formula (A1).

In Scheme C, step a, the appropriate A-nor-Δ5-steroid-3-carboxylic acid ester derivative (A1) from Scheme A, step e, is treated with a base of a metal, such as a base of an alkali earth metal, to yield the corresponding ester enolate (6). The ester enolate (6) can optionally be converted to the corresponding silyl ketene acetal (6') by treatment with trimethylsilylchloride according to conventional procedures and techniques.

In step b, the ester enolate (6) or the silyl ketene acetal (6') is converted to the corresponding A-nor-Δ5-steroid-3-phenylselenide derivative (7) by treatment with phenylselenylhalide, such as phenylselenylchloride or phenylselenylbromide. Phenylselenylbromide is preferred.

In step c, the corresponding A-nor-$\Delta^5$-steroid-3-phenylselenide derivative (7) is converted to its selenoxide and then hydrolyzed to yield the corresponding A-nor-$\Delta^2,\Delta^5$-steroid-3-carboxylic acid ester derivative ($B_1$) by treatment with an oxidizing agent such as hydrogen peroxide or m-chloro-peroxybenzoic acid. The preferred oxidizing reagent is hydrogen peroxide.

Compounds of the formula ($B_1$) can be converted to their corresponding free acids by hydrolysis as described in Scheme A, step f and in Scheme B.

The following example presents a typical synthesis as described by Scheme C. These examples are understood to be illustrative only and are not intended to limit the scope of the invention in any way.

EXAMPLE 5

17$\beta$-(N,N-Diisopropylcarboxamide)-A-nor-androst-2,5-diene-3-carboxylic acid, methyl ester 5 Step a:

17$\beta$-(N,N-Diisopropyl-carboxamide)-A-nor-androst-5-ene-3-[lithio(methyl ester enolate)]

To a stirred solution of 17$\beta$-(N,N-diisopropyl-carboxamide)-A-nor-androst-5-ene-3$\alpha$-carboxylic acid, methyl ester (430 mg, 1.0 mmol), prepared from the corresponding acid and diazomethane, in dry THF (25 mL) under argon at $-70°$ C., add a solution of lithium diisopropylamide (1.1 mmol) in THF (11 mL) over 15 minutes. Stir at $-70°$ C. to provide the title compound.

Step b:

17$\beta$-(N,N-Diisopropyl-carboxamide)-A-nor-androst-5-ene-3-phenylselenide-3-carboxylic acid, methyl ester After stirring the reaction mixture of 17$\beta$-(N,N-diisopropyl-carboxamide)-A-nor-androst-5-ene-3-lithio[(-methyl ester enolate)] at $-70°$ C. for 15 minutes, add a solution of phenylselenyl bromide (260 mg, 1.1 mmol) in THF (5 mL) all at once. Allow the mixture to warm to 25° C. over 1 hour and then pour the mixture into a 1N HCl solution. Extract into dichloromethane and dry the organic layer over anhydrous MgSO$_4$. Concentrate in vacuo and flash chromatograph on a silica gel column eluting with 10% ethyl acetate in hexane to give the title compound.

Alternate Step b:

17$\beta$-(N,N-Diisopropyl-carboxamide)-A-nor-androst-5-ene-3-phenylselenide-3-carboxylic acid, methyl ester After stirring the reaction mixture of 17$\beta$-(N,N-diiso-propyl-carboxamide)-A-nor-androst-5-ene-3-lithio[(-methyl ester enolate)] at $-70°$ C. for 15 minutes, add chlorotrimethylsilane (140 $\mu$L, 1.1 mmol) via a syringe. Allow the mixture to warm to 25° C. over 30 minutes and then concentrate in vacuo. Take the residue up in dry dichloromethane (25 mL), cool to 0° C. and treat the mixture with a solution of phenylselenyl bromide (260 mg, 1.1 mmol) in THF (5 mL). Allow the mixture to warm to 25° C. over 1 hour and then pour the mixture into a 1N HCl solution. Extract into dichloromethane and dry the organic layer over anhydrous MgSO$_4$. Concentrate in vacuo and flash chromatograph on a silica gel column eluting with 10% ethyl acetate in hexane to give the title compound.

Step c:

17$\beta$-(N,N-Diisopropylcarboxamide)-A-nor-androst-2,5-diene-3-carboxylic acid, methyl ester Dissolve 17$\beta$-(N,N-diisopropyl-carboxamide)-A-nor-androst-5-ene-3-phenylselenide-3-carboxylic acid, methyl ester in dry THF (20 mL) and treat with hydrogen peroxide in small portions until no selenides remain after TLC analysis. Warm the solution with stirring until no selenoxide remains by TLC analysis. Concentrate in vacuo and flash chromatograph on a silica gel column eluting with 10% ethyl acetate in hexane to give the title compound.

EXAMPLE 6

17$\beta$-(N,N-Diisopropylcarboxamide)-A-nor-androst-2,5-diene-3-carboxylic acid Method 1:

Dissolve 17$\beta$-(N,N-diisopropylcarboxamide)-A-nor-androst-5-diene-3-carboxylic acid, methyl ester (100 mg, 0.233 mmol) in methylene chloride (3 mL) and treat with trimethylsiliyl iodide (78 mg, 0.5 mmol). When the reaction is complete, pour the reaction mixture into buffer and separate the organic phase. Wash the organic phase with well with water, dry (MgSO$_4$) and evaporate the solvent in vacuo. Purify by silica gel chromatography to give the title compound.

Method 2:

Dissolve 17$\beta$-(N,N-diisopropylcarboxamide)-A-nor-androst-2,5-diene-3-carboxylic acid, methyl ester (100 mg, 0.223) in ethanol (4 mL) and treat with lithium hydroxide (42 mg, 10 mmol) and water (1 mL). Stir under nitrogen atmosphere until hydrolysis is complete, evaporate the solvent, acidify with dilute hydrochloric acid and extract into ethyl acetate. Separate the organic phase, extract the aqueous phases with ethyl acetate (2X) and wash the combined organic phases with water, then with saturated sodium chloride. Dry (MgSO$_4$), evaporate the solvent in vacuo and purify by silica gel chromatography to give the title compound.

EXAMPLE 7

17$\beta$-(N-t-Butylcarboxamide)-A-nor-androst-2,5-diene-3-carboxylic acid, isopropyl ester Step a:

17$\beta$-(N-t-Butylcarboxamide)-A-nor-androst-5-ene-3-lithio(isopropyl ester enolate)]

To a stirred solution of 17$\beta$-(N-t-butylcarboxamide)-A-nor-androst-5-ene-3$\alpha$-carboxylic acid, isopropyl ester (Example 2, step e) (430 mg, 1.0 mmol) in dry THF (25 mL) under argon at $-70°$ C., add a solution of lithium diisopropylamide (1.1 mmol) in THF (11 mL) over 15 minutes. Stir at $-70°$ C. to provide the title compound.

Step b:

17$\beta$-(N-t-Butylcarboxamide)-A-nor-androst-5-ene-3-phenylselenide-3-carboxylic acid, isopropyl ester After stirring the 17$\beta$-(N-t-butylcarboxamide)-A-nor-androst-5-ene-3-[lithio(isopropyl ester enolate)] at $-70°$ C. for minutes, add a solution of phenylselenyl bromide (260 mg, 1.1 mmol) in THF (5 mL) all at once. Allow the mixture to warm to 25° C. over 1 hour and then pour the mixture into a 1N HCl solution. Extract into dichloromethane and dry the organic layer over anhydrous MgSO$_4$. Concentrate in vacuo and flash chromatograph on a silica gel column eluting with 10% ethyl acetate in hexane to give the title compound.

Alternate Step b:

17β-(N-t-Butylcarboxamide)-A-nor-androst-5-ene-3-phenylselenide-3-carboxylic acid, isopropyl ester After stirring the 17β-(N-t-butylcarboxamide)-A-nor-androst-5-ene-3-[lithio(isopropyl ester enolate)] at −70° C. for 15 minutes, add chlorotrimethylsilane (140 μL, 1.1 mmol) via a syringe. Allow the mixture to warm to 25° C. over 30 minutes and then concentrate in vacuo. Take the residue up in dry dichloromethane (25 mL), cool to 0° C. and treat the mixture with a solution of phenylselenyl bromide (260 mg, 1.1 mmol) in THF (5 mL). Allow the mixture to warm to 25° C. over 1 hour and then pour the mixture into a 1N HCl solution. Extract into dichloromethane and dry the organic layer over anhydrous MgSO$_4$. Concentrate in vacuo and flash chromatograph on a silica gel column eluting with 10% ethyl acetate in hexane to give the title compound.

Step c:

17β-(N-t-Butylcarboxamide)-A-nor-androst-2,5-diene-3-carboxylic acid, isopropyl ester Dissolve the 17β-(N-t-butylcarboxamide)-A-nor-androst-5-ene-3-phenylselenide-3-carboxylic acid, isopropyl ester in dry THF (20 mL) and treat with hydrogen peroxide in small portions until no selenides remain after TLC analysis. Warm the solution with stirring until no selenoxide remains by TLC analysis. Concentrate in vacuo and flash chromatograph on a silica gel column eluting with 10% ethyl acetate in hexane to give the title compound.

EXAMPLE 8

17β-(N-t-Butylcarboxamide)-A-nor-androst-2,5-diene-3-carboxylic acid

Method 1:

Dissolve 17β-(N-t-butylcarboxamide)-A-nor-androst-2,5-diene-3-carboxylic acid, isopropyl ester (100 mg, 0.233 mmol) in methylene chloride (3 mL) and treat with trimethylsiliyl iodide (78 mg, 0.5 mmol). When the reaction is complete, pour the reaction mixture into buffer and separate the organic phase. Wash the organic phase with well with water, dry (MgSO$_4$) and evaporate the solvent in vacuo. Purify by silica gel chromatography to give the title compound.

Method 2:

Dissolve 17β-(N-t-butylcarboxamide)-A-nor-androst-2,5-diene-3-carboxylic acid, isopropyl ester (100 mg, 0.2 mmol) in ethanol (4 mL) and treat with lithium hydroxide (42 mg, 10 mmol) and water (1 mL). Stir under nitrogen atmosphere until hydrolysis is complete, evaporate the solvent, acidify with dilute hydrochloric acid and extract into ethyl acetate. Separate the organic phase, extract the aqueous phases with ethyl acetate (2X) and wash the combined organic phases with water, then with saturated sodium chloride. Dry (MgSO$_4$), evaporate the solvent in vacuo and purify by silica gel chromatography to give the title compound..

The following compounds can be prepared by procedures analogous to those described in Example 5-8:

20α-(hydroxymethyl)-A-nor-pregn-2,5-diene-3-carboxylic acid;
20α-(hydroxymethyl)-A-nor-pregn-2,5,11-triene-3-carboxylic acid;
A-nor-pregn-2,5-diene-20-one-3-carboxylic acid;
A-nor-pregn-2,5,11-triene-20-one-3-carboxylic acid;
17β-(N-tertiarybutylcarboxamide)-A-nor-androst-2,5,11-triene-3-carboxylic acid;
17β-(N,N-diisopropylcarboxamide)-A-nor-androst-2,5,11-triene-3-carboxylic acid.

A general synthetic procedure for the preparation of steroid derivatives of formula (C) is set forth in Scheme D. In Scheme D, all substituents are as previously defined.

SCHEME D

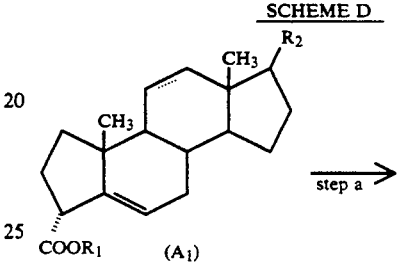

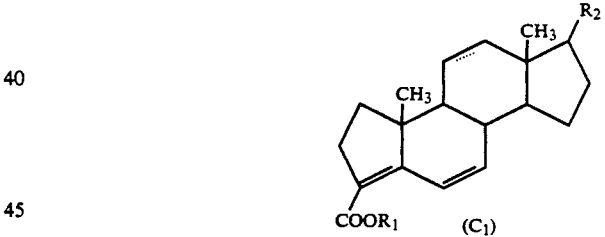

In general, a steroid derivative of formula (C) can be prepared from a steroid derivative of Formula (A$_1$) in a two-step process.

In step a, the olefin functionality of the appropriate A-nor-Δ$^5$-steroid-3-carboxylic acid ester derivative of formula (A$_1$) can be converted to the corresponding dibromo steroid derivative of structure (8). For example, the A-30 nor-Δ$^5$-steroid-3-carboxylic acid ester derivative of formula (A$_1$) with pyridinium bromide perbromide, in a suitable aprotic solvent, such as methylene chloride.

In step b, the dibromo steroid derivative of structure (8) is converted to the corresponding diene steroid derivative of formula (Cl). For example, the appropriate dibromo steroid derivative of structure (8) can be dehydrohalo-genated with an appropriate non-nucleophilic base, such as 1,8-diazabicyclo[5.4.0]undecene-7 (DBU).

Of course, compounds of the formula (C$_1$) can be converted to their corresponding free acids by hydrolysis as described in Scheme A, step f or as described in Scheme B.

The following examples represent typical syntheses as described in Scheme D. These examples are understood to be illustrative only and are not intended to limit the scope of the present invention in any way.

EXAMPLE 9

17$\beta$-(N,N-Diisopropylcarboxamide)-A-nor-androst-3,6-diene-3-carboxylic acid, methyl ester

Step a and Step b:

Dissolve 17$\beta$-(N,N-diisopropyl-carboxamide)-A-nor-androst-5-ene-3$\alpha$-carboxylic acid, methyl ester (50 mg, 0.11 mmol) in methylene chloride (2 mL) and treat the pyridinium bromide perbromide (35 mg, 0.1 mmol). Stir at room temperature for 1.2 hours. Add DBU (0.5 mL) and heat at 50° C. for 2 hours. Cool, pour into a mixture of dilute hydrochloric acid and methylene chloride. Separate the organic phase, dry (MgSO$_4$) and evaporate the solvent in vacuo to give 35 mg of the title compound.

EXAMPLE 10

17$\beta$-(N,N-Diisopropylcarboxamide)-A-nor-androst-3,6-diene-3-carboxylic acid

Method 1:

Dissolve 17$\beta$-(N,N-diisopropylcarboxamide)-A-nor-androst-3,6-diene-3-carboxylic acid, methyl ester (100 mg, 0.233 mmol) in methylene chloride (3 mL) and treat with trimethylsiliyl iodide (78 mg, 0.5 mmol). When the reaction is complete, pour the reaction mixture into buffer and separate the organic phase. Wash the organic phase with well with water, dry (MgSO$_4$) and evaporate the solvent in vacuo. Purify by silica gel chromatography to give the title compound.

Method 2:

Dissolve 17$\beta$-(N,N-diisopropylcarboxamide)-A-nor-androst-3,6-diene-3-carboxylic acid, methyl ester (35 mg) in methanol (5 mL) and treat with 1N lithium hydroxide (0.5 mL) and solid lithium hydroxide (50 mg). Stir under nitrogen atmosphere for 12 hours. Dilute with water, filter over Celite, and acidify with acetic acid (0.5 mL). Filter, acidify the mother liquors with dilute hydrochloric acid and extract into ethyl acetate. Separate the organic phase, extract the aqueous phases with ethyl acetate and wash the combined organic phases with water, then with saturated sodium chloride. Dry (MgSO$_4$), evaporate the solvent in vacuo and purify by silica gel chromatography to give the title compound.

NMR-ppm $\delta$ (CDCl$_3$) 300MHz: 7.06 (dd, 1H, J$_1$=10Hz, J$_2$=3Hz); 6.07 (bd, J$_d$=10Hz); 4.21 (h, 1H, J=7Hz); 3.41 (h, 1H, J=7Hz); 1.43 (d, 3H, J=7Hz); 1.39 (d, 3H, J=7Hz); 1.23 (d, 3H, J=7Hz); 1.16 (d, 3H, J=7Hz); 0.97 (s, 3H); 0.86 (s, 3H).

EXAMPLE 11

17$\beta$-(N-t-Butylcarboxamide)-A-nor-androst-3,6-diene-3-carboxylic acid, isopropyl ester

Step a and Step b:

Dissolve 17$\beta$-(N-t-butyl-carboxamide)-A-nor-androst-3,6-diene-3-carboxylic acid, isopropyl ester (50 mg, 0.11 mmol) in methylene chloride (2 mL) and treat the pyridinium bromide perbromide (35 mg, 0.11 mmol). Stir at room temperature for 2 hours. Add DBU (2 mL) to the solution and evaporate the solvent in vacuo. Heat to 50° C. for 2 hours, pour into dilute hydrochloric acid and extract into and evaporate the solvent in vacuo. Purify by silica gel chromatography to give 35 mg of the title compound.

NMR-ppm $\delta$ (CDCl$_3$) 300MHz: 7.03 (dd, 1H, J$_1$=10Hz, J$_2$=3Hz); 5.99 (bd, 1H, J$_d$=10Hz); 5.11 (bs, 1H); 5.08 (h, 1H, J=7Hz); 1.36 (s, 9H); 1.28 (d, 3H, J=7Hz); 1.26 (d, 3H, J=7Hz); 0.94 (s, 3H); 0.86 (s, 3H).

EXAMPLE 12

17$\beta$-(N-t-butylcarboxamide)-A-nor-androst-3,6-diene-3-carboxylic acid

Method 1:

Dissolve 17$\beta$-(N-t-butylcarboxamide)-A-nor-androst-3,6-diene-3-carboxylic acid, isopropyl ester (100 mg, 0.2 mmol) in methylene chloride (3 mL) and treat with trimethylsiliyl iodide (78 mg, 0.5 mmol). When the reaction is complete, pour the reaction mixture into buffer and separate the organic phase. Wash the organic phase with well with water, dry (MgSO$_4$) and evaporate the solvent in vacuo. Purify by silica gel chromatography to give the title compound.

Method 2:

Dissolve 17$\beta$-(N-t-butylcarboxamide)-A-nor-androst-3,6-diene-3$\alpha$-carboxylic acid, isopropyl ester (35 mg) in methanol (5 mL) and treat with 1N lithium hydroxide (0.5 mL) and with solid lithium hydroxide (30 mg). Reflux under nitrogen atmosphere for 4 hours, pour into dilute hydrochloric acid and extract into ethyl acetate. Separate the organic phase, extract the aqueous phases with ethyl acetate and wash the combined organic phases with water, then with saturated sodium chloride. Dry (MgSO$_4$), evaporate the solvent in vacuo and purify by silica gel chromatography (25% ethyl acetate/hexane) to give the title compound.

NMR-ppm $\delta$ (CDCl$_3$) 300MHz: 7.06 (dd, 1H, J$_1$=10Hz, J$_2$=3Hz); 6.05 (bd, 1H, J$_d$=10Hz); 5.11 (bs, 1H); 1.37 (s, 9H); 0.95 (s, 3H); 0.86 (s, 3H).

The following compounds can be prepared by procedures analogous to those described in Examples 9–12:

20$\alpha$-(hydroxymethyl)-A-nor-pregn-3,6-diene-3-carboxylic acid;

20$\alpha$-(hydroxymethyl)-A-nor-pregn-3,6,11-triene-3-carboxylic acid;

A-nor-pregn-3,6-diene-20-one-3-carboxylic acid;

A-nor-pregn-3,6,11-triene-20-one-3-carboxylic acid;

17$\beta$-(N-tertiarybutylcarboxamide)-A-nor-androst-3,6,11-triene-3-carboxylic acid; 17$\beta$-(N,N-diisopropylcarboxamide)-A-nor-androst-3,6,11-triene-3-carboxylic acid;

In a further embodiment, the present invention provides a method for treating a patient afflicted with a DHT-mediated disease or condition comprising administering to said patient an effective 5-$\alpha$-reductase inhibitory amount of a compound of formula (A), (B), (C), (D).

As used herein, the term "patient" refers to a warm-blooded animal, such as a human, which is afflicted with a DHT-mediated disease or condition. DHT-mediated diseases or conditions are diseases or conditions which are associated with elevated androgen activity due to the excessive formation of DHT. DHT-mediated diseases or conditions include those such as acne, acne vulgaris, benign prostatic hypertrophy, androgenetic alopecia (common baldness caused by androgen in genetically susceptible men and women), seborrhea and female hirsutism.

Inhibition of steroid 5-α-reductase in a patient afflicted with a DHT-mediated disease or condition will effect an alleviation or control of the manifestations of the disease or condition by reducing the level of DHT in the affected tissue. As used herein, the term "alleviation or control of the manifestations of the disease or condition" refers to slowing, interrupting, arresting or stopping the disease manifestations and does not necessarily indicate a total elimination of the disease. The affected tissue is that tissue in which DHT levels are excessively elevated so as to result in the DHT-mediated disease or condition.

For example, in acne, DHT levels of skin tissue are elevated. Manifestations of acne include skin eruptions and lesions. Inhibition of skin 5-α-reductase will reduce DHT levels and control these manifestations of acne. In benign prostatic hypertrophy, DHT levels in the prostate are elevated. Manifestations of benign prostatic hypertrophy include the growth of the prostate gland. Inhibition of prostate 5-α-reductase will reduce DHT levels and control the growth of the prostate.

It is of course understood that patients may be treated for these DHT-mediated diseases or conditions either therapeutically or prophylactically. One skilled in the art of medical diagnosis will readily be able to ascertain those patients who are afflicted with a DHT-mediated disease or condition.

An effective 5-α-reductase inhibitory amount of a compound of formula (A), (B), (C), (D) refers to an amount of the compound which is effective, upon single or multiple dose administration to the patient, in inhibiting 5-α-reductase or reducing DHT in the tissue in which the DHT-mediated disease or condition is manifested. For example, in acne, an effective 5-α-reductase inhibitory amount of a compound of formula (A), (B), (C), (D) or refers to an amount of the compound which is effective in inhibiting 5-α-reductase activity in skin or in reducing DHT levels in skin. In prostatic hypertrophy, an effective 5-α-reductase inhibitory amount of a compound of formula (A), (B), (C), (D) or refers to an amount of the compound which is effective in inhibiting 5-α-reductase activity in the prostate or in reducing DHT levels in the prostate.

A therapeutically effective amount of a compound of formula (A), (B), (C), (D) or is expected to vary from about 0.1 milligram per kilogram of body weight per day (nag/kg/day) to about 400 mg/kg/day. Preferred amounts are expected to vary from about 0.1 to about 200 mg/kg/day.

In effecting treatment of a patient afflicted with a disease state described above, a compound of formula (A), (B), (C), (D) or can be administered in any form or mode which makes the compound bioavailable in effective amounts, including oral and parenteral routes. For example, compounds of formula (A), (B), (C), (D) or can be administered orally, subcutaneously, intramuscularly, intravenously, transdermally, intranasally, rectally, and the like. Oral or transdermal administration are generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable salts for purposes of stability, convenience of crystallization, increased solubility and the like.

In another embodiment, the present invention provides compositions comprising a compound of formula (A), (B), (C), (D) or in admixture or otherwise in association with one or more inert carriers These compositions are useful, for example, as assay standards, as convenient means of making bulk shipments, or as pharmaceutical compositions. An assayable amount of a compound of formula (A), (B), (C), (D) or is an amount which is readily measurable by standard assay procedures and techniques as are well known and appreciated by those skilled in the art. Assayable amounts of a compound of formula (A), (B), (C), (D) or will generally vary from about 0.001% to about 75% of the composition by weight. Inert carriers can be any material which does not degrade or otherwise covalently react with a compound of formula (A), (B), (C), (D) or. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of formula (A), (B), (C), (D) or in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, topical creams or gels, suppositories, solution, suspensions, or the like.

The compounds of the present invention may be administered orally, for example, with an inert diluent or with an edible carrier. They may be enclosed in gelatin capsules or compressed into tablets. For the purpose of oral administration, the compounds may be incorporated with excipients and used in the form of tablets, troches, gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 0.1–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 0.5 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (A), (B), (C), (D) or in their end-use application.

The preferred compounds of the present invention are those for which $R_1$ is hydrogen. Also preferred are those compounds of the present invention for which $R_2$ is 1-(hydroxymethyl)ethyl, N,N-diisopropylcarboxamide, N-tertiarybutylcarboxamide and 1-oxoethyl.

What is claimed is:

1. A compound of the formula

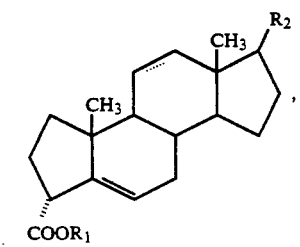 (A)

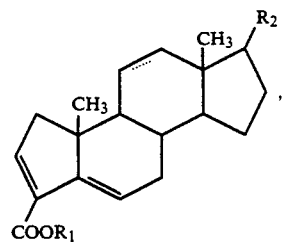 (B)

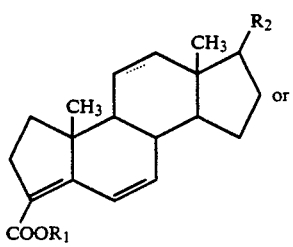 (C)

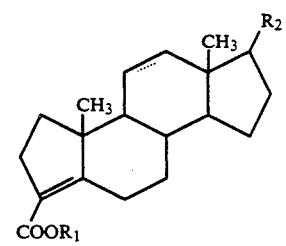 (D)

wherein
the dotted line represents an optional double bond;
$R_1$ is hydrogen, $C_1$-$C_6$ alkyl/cycloalkyl or —$(CH_2)_x$-Ar-$(M)_y$, wherein x is 0, 1 or 2; Ar is phenyl, y is 0, 1 or 2, and M is $C_1$-$C_6$ alkoxy, halogen, $C_1$-$C_6$ alkyl/cycloalkyl, or —$S(O)_zR_5$ wherein $R_5$ is a $C_1$-$C_6$ alkyl/cycloalkyl and z is 0, 1 or 2; and
$R_2$ is $C_1$-$C_6$ alkyl alcohol; $C_1$-$C_6$ alkyl aldehyde/ketone; $CON(R_3)(R_4)$, wherein $R_3$ and $R_4$ are each independently, hydrogen or $C_1$-$C_6$ alkyl/cycloalkyl, or —$(CH_2)_x$-Ar-$(M)_y$, wherein x is 0, 1 or 2, Ar is phenyl, y is 0, 1 or 2, and M is $C_1$-$C_6$ alkoxy, halogen, $C_1$-$C^6$ alkyl, or —$S(O)_zR_5$ wherein $R_5$ is a $C_1$-$C_6$ alkyl/cycloalkyl and z is 0, 1 or 2.

2. A compound of claim 1 wherein $R_1$ is hydrogen.

3. A compound of claim 2 wherein $R_2$ is 1-(hydroxymethyl)ethyl.

4. A compound of claim 2 wherein $R_2$ is N,N-diisopropylcarboxamide.

5. A compound of claim 2 wherein $R_2$ is N-tertiarybutylcarboxamide.

6. A method of treating a patient afflicted with a DHT-mediated disease or condition comprising administering to said patient an effective 5-α-reductase inhibitory amount of a compound of claim 1.

7. A pharmaceutical composition comprising an effective 5-α-reductase inhibitory amount of a compound of claim 1 in admixture with one or more pharmaceutically acceptable carriers or excipients.

8. A compound of claim 1 wherein the compound is 17β-(N,N-diisopropylcarboxamide)-A-nor-androst-5-ene-3α-carboxylic acid.

9. A compound of claim 1 wherein the compound is 2  17β-(N,N-diisopropylcarboxamide)-A-nor-androst-3,6-diene-3-carboxylic acid.

10. A compound of claim 1 wherein the compound is 17β-(N,N-diisopropylcarboxamide)-A-nor-androst-2,5-diene-3-carboxylic acid.

11. A compound of claim 1 wherein the compound is 17β-(N,N-diisopropylcarboxamide)-A-nor-androst-3-ene-3-carboxylic acid.

12. A compound of claim 1 wherein the compound is 17β-(N-tertiarybutylcarboxamide)-A-nor-androst-5-ene-3α-carboxylic acid.

13. A compound of claim 1 wherein the compound is 17β-(N-tertiarybutylcarboxamide)-A-nor-androst-3,6-diene-3-carboxylic acid.

14. A compound of claim 1 wherein the compound is 17β-(N-tertiarybutylcarboxamide)-A-nor-androst-2,5-diene-3-carboxylic acid.

15. A compound of claim 1 wherein the compound is 17β-(N-tertiarybutylcarboxamide)-A-nor-androst-3-ene-3-carboxylic acid.

* * * * *

UNITED STATES PATENT AND TRADEMARK OFFICE
CERTIFICATE OF CORRECTION

PATENT NO. : 5,100,917
DATED : March 31, 1992
INVENTOR(S) : Gary A. Fynn, et. al.

It is certified that error appears in the above-indentified patent and that said Letters Patent is hereby corrected as shown below:

Column 2, line 42 reads " - $Si(O)_zR_5$ wherein", should read -- $-S(O)_zR_5$ wherein --.

Column 3, line 17 ( reads "-$CH(OH)CH_2CH(CH_3)_z$;", should read -- -$CH(OH)CH_2CH(CH_3)_2$; --.

Column 3, line 40 reads "refers to a hydrogen,", should read -- refers to a carboxamide group wherein $R_3$ and $R_4$ are each independently, hydrogen, --.

Column 8, line 9 reads "5-ene-3o-carboxylic", should read -- 5-ene-3α-carboxylic --.

Column 9, line 30 reads "1.37 (s,9);", should read --1.37 (s9H);--.

Column 11, line 12 reads "-3o-carboxylic acid", should read -- -3α-carboxylic acid --.

Column 14, line 21 reads " androst-5-diene-3-", should read -- androst-2,5-diene-3- --.

Column 14, line 65 reads " for minutes, add a solution", should read -- for 15 minutes, add a solution.

Column 16, line 1 & 2 reads "-diene-3-carboylic", should read -- -diene-3α-carboxylic --.

Column 16, line 55 reads "the A-30 nor -$\Delta^5$-", should read -- the A-nor-$\Delta^5$- --.

Column 18, line 1 reads "into and evaporate the solvent in vacuo.", should read -- into methylene chloride. Separate the organic phase, dry (Mg SO4) and evaporate the solvent *in vacuo*. --.

Column 20, line 55 (page 35, line 2) reads "tablets, troches, gums and the like.", should read -- tablets, troches, capsules, elixirs, suspensions, syrups, wafers, chewing gums and the like. --.

Column 22. line 45 (page 38, line 30) reads " halogen, $C_1$-$C^6$ alkyl,", should read -- halogen, $C_1$-$C_6$ alkyl/cycloalkyl,--

Column 22, line 66 (page 39, claim 9) reads " compound is 2 17β-", should read -- compound is 17β- --.

Signed and Sealed this

Thirtieth Day of August, 1994

Attest:

BRUCE LEHMAN

Attesting Officer

Commissioner of Patents and Trademarks